(12) United States Patent
Hashimoto et al.

(10) Patent No.: US 11,197,730 B2
(45) Date of Patent: Dec. 14, 2021

(54) MANIPULATOR SYSTEM

(71) Applicant: KAWASAKI JUKOGYO KABUSHIKI KAISHA, Kobe (JP)

(72) Inventors: Yasuhiko Hashimoto, Kobe (JP); Nobuyasu Shimomura, Kobe (JP); Tsuyoshi Maehara, Itami (JP); Masayuki Kamon, Akashi (JP); Shigetsugu Tanaka, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 457 days.

(21) Appl. No.: 15/755,135

(22) PCT Filed: May 27, 2016

(86) PCT No.: PCT/JP2016/002582
§ 371 (c)(1),
(2) Date: Feb. 26, 2018

(87) PCT Pub. No.: WO2017/033355
PCT Pub. Date: Mar. 2, 2017

(65) Prior Publication Data
US 2018/0257238 A1 Sep. 13, 2018

(30) Foreign Application Priority Data

Aug. 25, 2015 (JP) .............................. JP2015-165479

(51) Int. Cl.
*G05B 15/00* (2006.01)
*G05B 19/00* (2006.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ........ B25J 19/04; B25J 19/023; B25J 9/1661; B25J 9/1646; B25J 9/0081; B25J 13/087;
(Continued)

(56) References Cited

U.S. PATENT DOCUMENTS

| 4,942,538 A | 7/1990 | Yuan et al. |
| 6,278,906 B1 * | 8/2001 | Piepmeier .............. B25J 9/1607 700/245 |

(Continued)

FOREIGN PATENT DOCUMENTS

| CN | 1903522 A | 1/2007 |
| EP | 1110854 A2 | 6/2001 |

(Continued)

*Primary Examiner* — B M M Hannan
(74) *Attorney, Agent, or Firm* — Oliff PLC

(57) ABSTRACT

A manipulator system configured to perform a work to a workpiece being moved by a moving device, includes a robotic arm, having one or more joints and to which a tool configured to perform the work to the workpiece is attached, an operating device configured to operate the robotic arm, a first imaging means configured to image the workpiece, while following the movement of the workpiece, a second imaging means fixedly provided in a work area to image a situation of the work to the workpiece, a displaying means configured to display an image imaged by the first imaging means and an image imaged by the second imaging means, and a control device configured to control the operation of the robotic arm based on an operating instruction of the operating device, while detecting a moving amount of the workpiece being moved by the moving device and carrying out a tracking control of the robotic arm according to the moving amount of the workpiece.

9 Claims, 9 Drawing Sheets

(51) Int. Cl.
| | |
|---|---|
| *B25J 13/00* | (2006.01) |
| *A61B 34/37* | (2016.01) |
| *G05B 19/418* | (2006.01) |
| *B25J 9/00* | (2006.01) |
| *B25J 9/16* | (2006.01) |
| *B23P 19/04* | (2006.01) |
| *B25J 19/04* | (2006.01) |
| *B25J 13/08* | (2006.01) |
| *B25J 3/00* | (2006.01) |
| *B25J 13/06* | (2006.01) |
| *B25J 18/00* | (2006.01) |
| *B25J 19/02* | (2006.01) |
| *B25J 3/04* | (2006.01) |
| *B23Q 15/12* | (2006.01) |
| *B25J 13/02* | (2006.01) |
| *B25J 11/00* | (2006.01) |
| *G06F 3/01* | (2006.01) |
| *H04N 5/232* | (2006.01) |
| *H04N 7/18* | (2006.01) |
| *A61B 34/32* | (2016.01) |
| *G06T 7/62* | (2017.01) |
| *G06T 7/70* | (2017.01) |
| *B23P 21/00* | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ...... B25J 13/085; B25J 9/1602; B25J 19/028; B25J 9/1612; B25J 9/1674; B25J 9/1653; B25J 13/084; B25J 13/025; B25J 13/065; B25J 13/003; B25J 11/008; B25J 9/163; B25J 13/02; B25J 9/1628; B25J 9/1633; B25J 3/04; B25J 9/1689; B25J 9/1682; B25J 9/1664; B25J 9/161; B25J 18/00; B25J 13/088; B25J 13/06; B25J 9/1669; B25J 3/00; B25J 13/08; B25J 13/006; B25J 9/1697; B25J 9/0084; B25J 13/00; B25J 9/126; B25J 19/06; B25J 19/02; B25J 11/005; B25J 9/1692; G05B 2219/33056; G05B 2219/40202; G05B 19/42; G05B 2219/39083; G05B 2219/37565; G05B 2219/3755; G05B 19/4182; G05B 2219/40136; G05B 2219/40162; G05B 2219/40195; G05B 2219/40134; G05B 2219/40183; G05B 2219/40169; G05B 2219/33007; G05B 2219/40142; G05B 2219/35464; G05B 2219/39533; G05B 2219/40163; G05B 2219/39531; G05B 2219/40022; G05B 2219/39439; G05B 2219/40627; G05B 2219/40146; G05B 2219/40161; G05B 2219/40139; G05B 2219/40387; G05B 2219/40145; G05B 2219/40182; G05B 2219/39004; G05B 2219/40143; G05B 2219/39102; G05B 2219/37297; A61B 34/37; A61B 34/32; A61B 34/70; A61B 34/35; Y10S 901/03; Y10S 901/02; Y10S 901/46; Y10S 901/10; Y10S 901/41; Y10S 901/27; Y10S 901/08; Y10S 901/47; Y10S 901/09; B23Q 15/12; B23P 19/04; B23P 21/002; B23P 21/00; G06T 7/70; G06T 7/62; H04N 7/181; H04N 5/23219; G06F 3/017
USPC .................................................. 700/245–262
See application file for complete search history.

(56) References Cited

U.S. PATENT DOCUMENTS

| | | | | |
|---|---|---|---|---|
| 6,313,595 | B2 * | 11/2001 | Swanson | B25J 9/1679 318/568.11 |
| 7,138,780 | B2 * | 11/2006 | Stahs | B23Q 7/007 318/568.11 |
| 8,010,233 | B2 * | 8/2011 | Hashimoto | G06T 1/00 700/245 |
| 9,333,654 | B2 * | 5/2016 | Chen | B25J 9/1697 |
| 2003/0208302 | A1 * | 11/2003 | Lemelson | G05B 19/19 700/245 |
| 2006/0091842 | A1 * | 5/2006 | Nishiyama | G05B 19/4183 318/568.11 |
| 2006/0111810 | A1 * | 5/2006 | Kim | B25J 19/0091 700/186 |

(56) References Cited

U.S. PATENT DOCUMENTS

| | | | | |
|---|---|---|---|---|
| 2006/0113945 A1* | 6/2006 | Stahs | B23Q 7/007 | 318/568.11 |
| 2007/0007924 A1* | 1/2007 | Nishihara | B25J 9/0093 | 318/560 |
| 2007/0073439 A1* | 3/2007 | Habibi | G06T 7/246 | 700/213 |
| 2007/0075048 A1* | 4/2007 | Kunisaki | B25J 9/1697 | 219/91.1 |
| 2007/0079503 A1* | 4/2007 | Lee | B62D 65/06 | 29/787 |
| 2007/0179671 A1 | 8/2007 | Arimatsu et al. | | |
| 2008/0312769 A1* | 12/2008 | Sato | B25J 9/1687 | 700/249 |
| 2010/0008754 A1* | 1/2010 | Hartmann | G05B 19/4103 | 414/800 |
| 2010/0017033 A1 | 1/2010 | Boca | | |
| 2011/0010012 A1* | 1/2011 | Murayama | G05B 19/423 | 700/260 |
| 2011/0082586 A1* | 4/2011 | Nishihara | B25J 9/1697 | 700/259 |
| 2011/0087360 A1* | 4/2011 | Chen | B25J 9/1697 | 700/114 |
| 2012/0277898 A1* | 11/2012 | Kawai | B25J 9/1697 | 700/114 |
| 2012/0323357 A1* | 12/2012 | Izumi | G05B 19/4182 | 700/228 |
| 2013/0329954 A1* | 12/2013 | Ikeda | B23Q 17/2414 | 382/103 |
| 2014/0372116 A1* | 12/2014 | Smith | B25J 13/003 | 704/235 |
| 2015/0251312 A1* | 9/2015 | Suzuki | B25J 9/163 | 700/250 |
| 2017/0021500 A1* | 1/2017 | Davis | B25J 9/1664 | |

FOREIGN PATENT DOCUMENTS

| | | |
|---|---|---|
| JP | H04-300173 A | 10/1992 |
| JP | H06-262545 A | 9/1994 |
| JP | H09-091015 A | 4/1997 |
| JP | 2003-311661 A | 11/2003 |
| JP | 2011093062 A | 5/2011 |

* cited by examiner

MANIPULATOR SYSTEM

TECHNICAL FIELD

The present disclosure relates to a manipulator system.

BACKGROUND ART

Conventionally, in control devices of an industrial manipulator, there is a technology in which the slave arm tracks a conveyor synchronizing with the motion of the flow of the conveyor (see Patent Documents 1 to 3).

REFERENCE DOCUMENTS OF CONVENTIONAL ART

Patent Documents

[Patent Document 1] JP1994-262545A
[Patent Document 2] JP1992-300173A
[Patent Document 3] JP2011-093062A

DESCRIPTION OF THE DISCLOSURE

Problems to be Solved by the Disclosure

Meanwhile, in recent years, it is proposed in terms of an improvement of productivity that a robot and a worker work jointly. For example, it is assumed that the robot is introduced into an assembly line of a product and a work, such as assembling, of a component, small processing, etc. to a machine (workpiece) which is conveyed on a conveyor belt. Especially, the robot is suitable for works, such as conveying of a weighted workpiece, which a human is not good at.

However, in the conventional technology, since a synchronous instruction value is calculated based on present coordinates of a slave arm hand part located above the conveyor, and a speed setting value of the conveyor, a control device is not able to accurately detect the position of the workpiece on the conveyor. Thus, there is room for an improvement in the accuracy of performing the work to the workpiece being conveyed on the conveyor. Such a problem is common to manipulator systems which perform a work to a workpiece which is moved by other moving devices, such as a positioner, other than the conveyor.

Therefore, one purpose of the present disclosure is to provide a manipulator system, capable of performing a work to a workpiece which is moved by a moving device, with sufficient accuracy.

Summary of the Disclousre

According to one aspect of the present disclosure, a manipulator system configured to perform a work to a workpiece being moved by a moving device is provided, which includes a robotic arm, having one or more joints and to which a tool configured to perform the work to the workpiece is attached, an operating device configured to operate the robotic arm, a first imaging means configured to image the workpiece, while following the movement of the workpiece, a second imaging means fixedly provided in a work area to image a situation of the work to the workpiece, a displaying means configured to display an image imaged by the first imaging means and an image imaged by the second imaging means, and a control device configured to control the operation of the robotic arm based on an operating instruction of the operating device, while detecting a moving amount of the workpiece being moved by the moving device and carrying out a tracking control of the robotic arm according to the moving amount of the workpiece.

With the above configuration, by detecting the moving amount of the workpiece being moved by the moving device, the robotic arm is able to accurately be tracking-controlled according to the moving amount of the workpiece. Meanwhile, since the workpiece seems to be stopped in the image imaged by the first imaging means (tracking camera) while following the movement of the workpiece, a worker can easily operate the tool with the operating device. Further, the worker can perform the work to the workpiece by operating the operating device, while checking the image imaged by the second imaging means (fixed camera). Therefore, the accuracy of the work improves. Note that the displaying means may display the image of the first imaging means and the image of the second imaging means simultaneously or switchingly.

The manipulator system may perform the work to the workpiece being moved by a conveyor or a positioner provided with one or more driving shafts. The control device may detect the moving amount of the workpiece based on a driving amount of the driving shaft of the conveyor or the positioner.

With the above configuration, by detecting the moving amount of the workpiece based on the driving amount of the driving shaft of the conveyor or the positioner, the robotic arm is able to accurately be tracking-controlled.

The first imaging means may be attached to a tip end of the robotic arm. With this configuration, the workpiece is imageable while the tip end of the robotic arm is tracking the workpiece.

The displaying means may switchingly display the image imaged by the first imaging means and the image imaged by the second imaging means.

The displaying means may switchingly display the image of the situation of the work to the workpiece imaged by the first imaging means while following the movement of the workpiece, and the image of the situation of the work to convey the workpiece between a given position and the moving device in the work area, imaged by the second imaging means.

The first imaging means may include a plurality of fixed cameras arrayed along the moving direction of the moving device. The displaying means may switchingly and sequentially display the images imaged by the plurality of fixed cameras so as to follow the movement of the workpiece.

Effect of the Disclosure

According to the present disclosure, the manipulator system capable of performing the work to the workpiece which is moved by the moving device with sufficient accuracy can be provided.

The purpose described above, other purposes, feature, and advantages of the present disclosure will be apparent from the following detailed description of suitable embodiments with reference to the accompanying drawings.

MODES FOR CARRYING OUT THE DISCLOSURE

Figure 1:
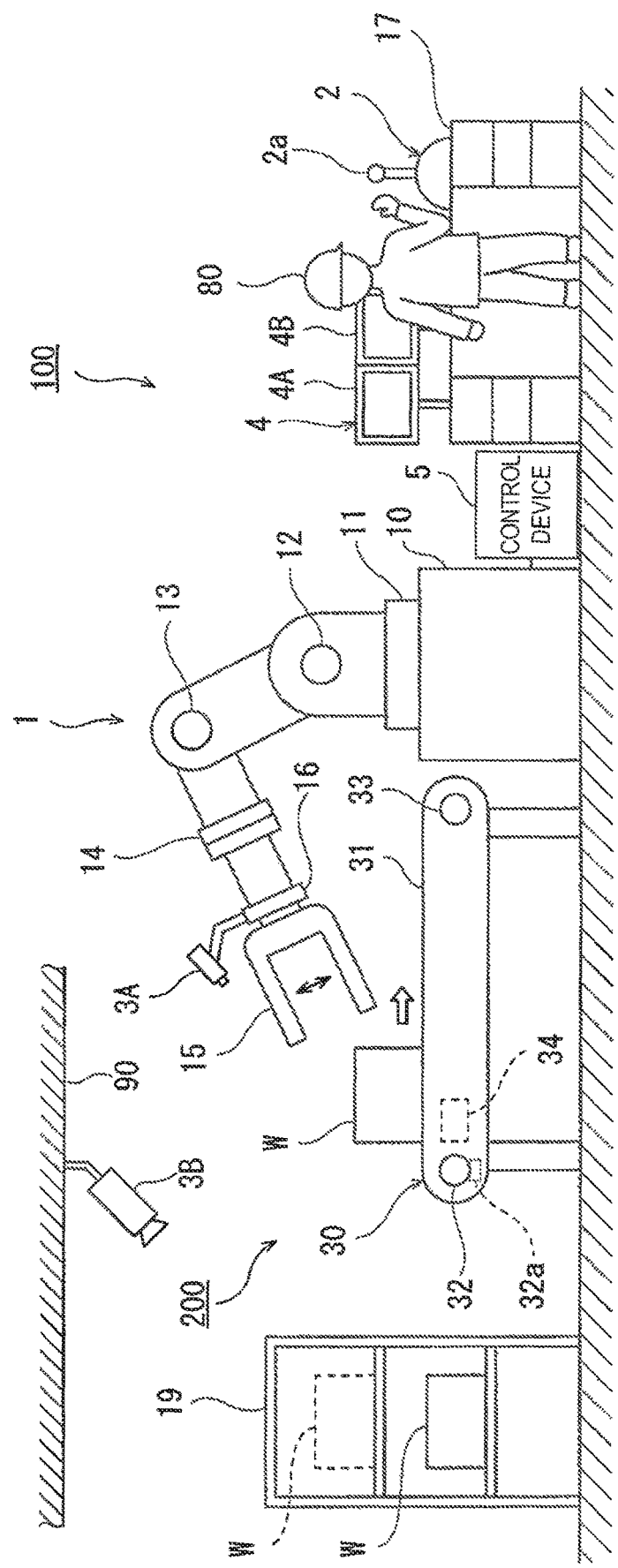
FIG. 1 is a schematic view illustrating a manipulator system according to a first embodiment.

Embodiments of the present disclosure will be described with reference to the drawings. Below, the same reference characters are assigned to the same or corresponding components throughout the drawings to omit redundant description.

First Embodiment

[Moving Device]

FIG. 1 is a schematic view illustrating a manipulator system according to a first embodiment. As illustrated in FIG. 1, the manipulator system 100 performs a work to a workpiece W which is moved by a moving device 30. In this embodiment, the moving device 30 is a conveyor which is disposed in a work area 200 and conveys the workpiece W in a fixed direction. The conveyor includes a conveyor belt 31 of endless-belt type, a driving pulley 32 around which one end side of the conveyor belt 31 is wound centering on a driving shaft, a driven pulley 33 around which the other end side of the conveyor belt 31 is wound centering on a driven shaft, and a conveyor control device 34. Note that the driving pulley 32 is provided with a motor (not illustrated) which rotates the driving pulley 32 through the driving shaft, and a conveyor encoder 32a which detects a driving amount of the driving shaft is attached to the motor. The conveyor control device 34 performs a feedback control of the motor according to a detection signal from the conveyor encoder 32a. The conveyor belt 31 circulates by the rotation of the driving pulley 32 which interlocks with the motor, and the workpiece W placed on the conveyor belt 31 is conveyed in the fixed direction (the arrow direction illustrated in FIG. 1). Note that, in this embodiment, although the motor drives at a constant speed, it may be driven intermittently or may accelerate or decelerate while driving.

In this embodiment, the work to the workpiece W is a work to carry the workpiece W which flows on the conveyor and store at a given position inside a storage shelf 19 for the workpiece W. In this embodiment, the workpiece W is a weighted workpiece, such as a metal component like a casing, metal material before fabrication, a die for manufacturing the metal component, and the like. That is, the manipulator system 100 performs a handling work of the weighted workpiece which a human is not good at. Note that the workpiece W is not be limited to the weighted workpiece, but may be a workpiece of 100 kg or less.

[Manipulator System]

The manipulator system 100 includes a robotic arm 1, an operating device 2, a first imaging means 3A, a second imaging means 3B, a displaying means 4, and a control device 5.

The robotic arm 1 has one or more joints, to which a tool 15 for performing the work to the workpiece W is attached. In this embodiment, the robotic arm 1 is provided on a pedestal 10 disposed in the work area 200, and has joints 11-14. Here, the joints 11 and 14 are torsional joints, and the joints 12 and 13 are bending joints. Each joint is provided with an actuator (not illustrated) comprised of a motor. The tool 15 is attached to a tool attaching part 16 of a flange shape at a tip end of the robotic arm 1.

In this embodiment, the tool 15 is a robot hand for gripping the workpiece W. The robot hand includes a hand main body attached to the tool attaching part 16 of the robotic arm 1, and two finger parts driven by an actuator (not illustrated), for example, comprised of a motor. When the actuator operates, the two finger parts move with respect to the hand main body. That is, the two finger parts of the robot hand are movable so as to approach or separate mutually, and are grippable of the workpiece W.

The operating device 2 is a device for operating the robotic arm 1. In this embodiment, the operating device 2 is disposed at a position distant from the work area 200 (outside of the work area 200), and is communicatably connected with the control device 5 in a wired or wireless manner. The operating device 2 includes a manipulandum 2a for being operated by a worker 80 located outside the work area 200, and a processor (not illustrated) into which operation data of the manipulandum 2a is inputted. The processor is configured to generate an operating instruction of the robotic arm 1 according to the operation data of the manipulandum 2a, and output it to the control device 5. The operating device 2 may be a mobile terminal, such as a smartphone or a tablet computer. Although the manipulandum 2a is a joystick here, it may be implemented by, for example, operation keys of the mobile terminal. In FIG. 1, the operating device 2 is disposed on the right side of a desk 17 so that the worker 80 is easy to operate it with his/her right hand.

The first imaging means 3A is a device for imaging the workpiece W, while moving to follow the workpiece W. In this embodiment, the first imaging means 3A is attached to the tool attaching part 16 at the tip end of the robotic arm 1. Here, the first imaging means 3A is oriented in such a direction that it images the situation in front of the tool 15.

The second imaging means 3B is fixedly provided in the work area 200 in order to image the situation of the work to the workpiece W. In this embodiment, the second imaging means 3B is fixedly installed on a ceiling 90 of the work area 200. Here, the second imaging means 3B is oriented in a direction toward the storage shelf 19, and images the situation of the work of the robot storing the workpiece W in the storage shelf 19. Note that a plurality of second imaging means 3B may be installed. In this case, for example, another second imaging means 3B may image the situation of the entire work area 200, or for example, may image the situation of the work to carry the workpiece W placed on a floor of the work area 200 to a given position on the conveyor. In this embodiment, the first imaging means 3A and the second imaging means 3B are comprised of a CCD (Charge Coupled Device) camera, respectively. Note that these imaging means may be comprised of a CMOS (Complementary Metal Oxide Semiconductor) camera etc. other than the CCD camera.

The displaying means 4 displays an image imaged by the first imaging means 3A and an image imaged by the second imaging means 3B. The displaying means 4 is comprised of a monitor 4A which displays the image of a tracking camera as the first imaging means 3A attached to the robotic arm 1, and a monitor 4B which displays the image of a fixed camera as the second imaging means 3B attached to the ceiling 90. The displaying means 4 may be configured to display the image of the tracking camera and the image of the fixed camera on a single monitoring screen. In this embodiment, although the displaying means 4 is the monitors, it may be a head-mounted display. Alternatively, the displaying means 4 may be configured integrally with the operating device 2. That is, the operating device 2 and the displaying means 4 may be implemented by, for example, an operation key and a monitor of a notebook PC or a mobile terminal.

Figure 2:
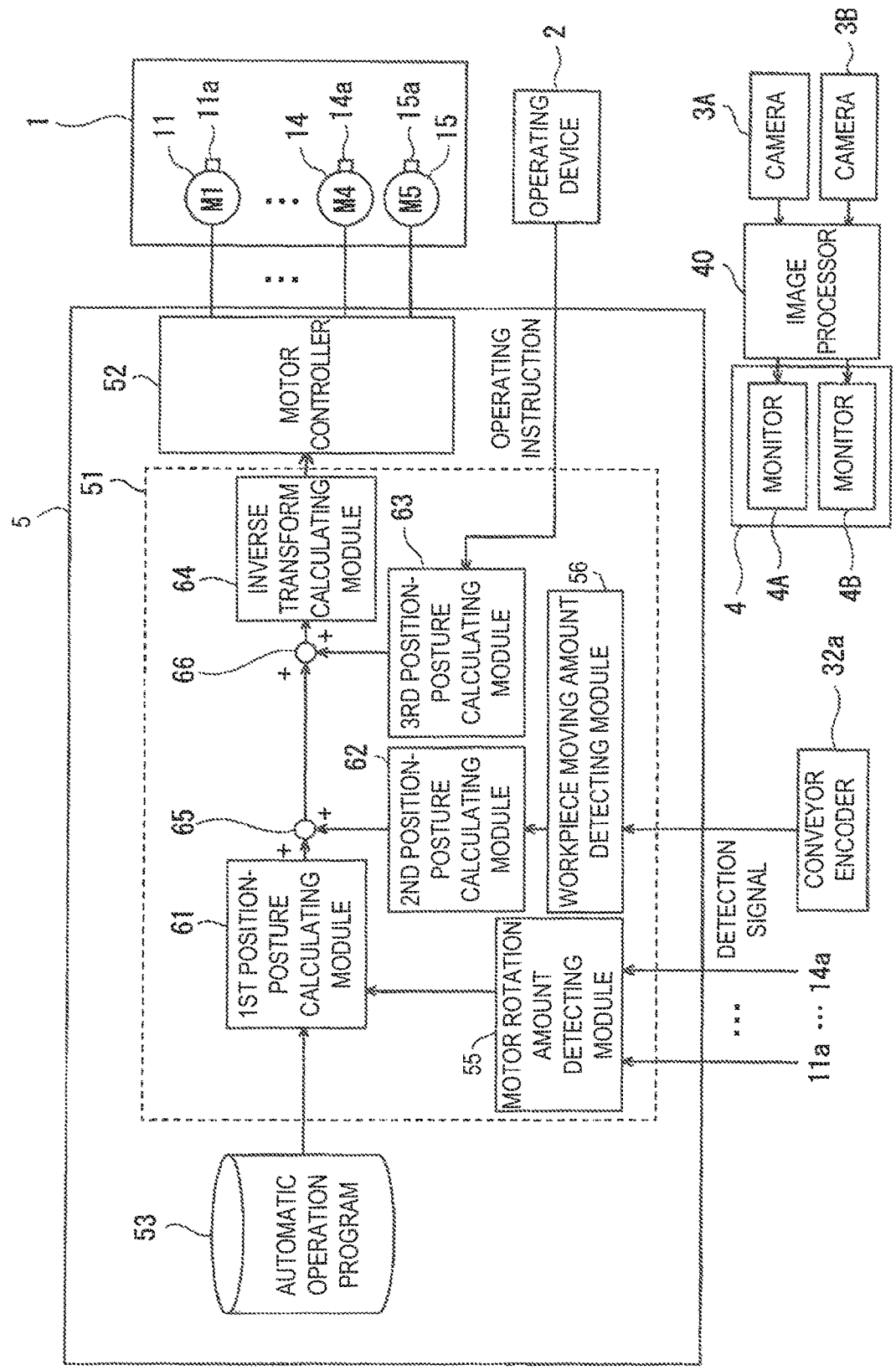
FIG. 2 is a block diagram illustrating a configuration of a control system of the manipulator system of FIG. 1.

The control device 5 is a robot controller which is connected with the robotic arm 1, the operating device 2, and the moving device 30, and controls the operation of the robotic arm 1 through an interface (not illustrated). The control device 5 is not limited to a single device, but may be comprised of a plurality of devices. In this embodiment, the control device 5 detects a moving amount of the workpiece W based on the driving amount of the driving shaft of the moving device 30, and controls the operation of the robotic arm 1 based the operating instruction of the operating device 2 while carrying out a tracking control of the robotic arm 1 according to the moving amount of the workpiece W. FIG. 2 is a block diagram illustrating a configuration of a control system of the manipulator system 100. As illustrated in FIG. 2, the control device 5 includes an arithmetic processor 51, a motor controller 52, and a memory 53, as well as an input/output interface and a communication interface (not illustrated). The memory 53 stores various operation programs and information for operating the robotic arm 1. For example, the robotic arm 1 operates automatically (hereinafter, referred to as "the automatic operation") by executing an automatic operation program. Here, motors M1-M5 which constitute the joints 11-14 and the robot hand (the tool 15) of the robotic arm 1 are provided with encoders 11a-15a for detecting rotation amounts of the motors. The encoders 11a-15a output detection signals according to the rotation amounts of the respective motors M1-M5 to the control device 5. Moreover, the conveyor encoder 32a outputs a detection signal indicative of the driving amount of the conveyor motor to the control device 5.

The arithmetic processor 51 includes a motor rotation amount detecting module 55, a workpiece moving amount detecting module 56, first to third position-posture calculating modules 61-63, an inverse transform calculating module 64, a first adder 65, and a second adder 66. Each of these parts is a functional block which is implemented by executing a given program in the arithmetic processor 51.

The motor rotation amount detecting module 55 detects the rotation amounts of the motors M1-M5 based on the detection signals inputted from the encoders 11a-14a, and outputs them to the first position-posture calculating module 61.

The workpiece moving amount detecting module 56 detects the moving amount of the workpiece W based on the detection signal inputted from the conveyor encoder 32a, and outputs it to the second position-posture calculating module 62.

The first position-posture calculating module 61 converts the instruction values of the respective motors M1-M4 based on the automatic operation program stored in the memory 53 into coordinates to calculate an instructing position (an X-coordinate value, a Y-coordinate value, and a Z-coordinate value) and a posture (an angle A, an angle O, and an angle T) at the tip end of the robotic arm 1 which are taught beforehand Here, the position at the tip end of the robotic arm 1 is a tool center point of the tool 15. Here, as variables related to the position, the X-coordinate value, the Y-coordinate value, and the Z-coordinate value which are coordinates of the tool center point are used. Moreover, as variables related to the posture, the angle A, the angle O, and the angle T (Euler angles) which are the posture of the tool 15 are used. That is, in this embodiment, the position and posture at the tip end of the robotic arm 1 are expressed by the six variables. Meanwhile, the first position-posture calculating module 61 converts the rotation amounts of the motors M1-M5 inputted from the motor rotation amount detecting module 55 to calculate the present position and posture at the tip end of the robotic arm 1. Then, the first position-posture calculating module 61 sets target values of the position and posture at the tip end of the robotic arm 1, and outputs them to the first adder 65.

The second position-posture calculating module 62 calculates moving amounts of the position and posture at the tip end of the robotic arm 1 (also referred to as "the workpiece tracking amount" of the robotic arm 1) based on the moving amount of the workpiece W inputted from the workpiece moving amount detecting module 56, and outputs them to the first adder 65.

The first adder 65 adds the workpiece tracking amount at the tip end of the robotic arm 1 to the target values of the position and posture at the tip end of the robotic arm 1, and outputs them to the second adder 66.

The third position-posture calculating module 63 calculates the moving amounts of the position and posture at the tip end of the robotic arm 1 (also referred to as "the operating amount" of the robotic arm 1) and the driving amount of the tool 15 (also referred to as "the operating amount" of the tool 15) based on the operating instruction of the robotic arm 1 inputted from the operating device 2, and outputs them to the second adder 66.

The inverse transform calculating module 64 inversely transforms the value obtained by adding the workpiece tracking amount and the operating amount to the target values at the tip end of the robotic arm 1 inputted from the second adder 66 by using a Jacobian matrix to calculate current instruction values of the respective motors M1-M5, and outputs them to the motor controller 52.

The motor controller 52 generates current based on the current instruction values inputted from the inverse transform calculating module 64, and supplies the generated current to the respective motors M1-M5. That is, the motor controller 52 is an amplifier which generates the drive current of the motors M1-M5 according to the current instruction values. Thus, the control device 5 is configured to control the operation of the robotic arm 1 based on the automatic operation program, the sensor signal of the conveyor encoder 32a, and the operating signal from the operating device 2.

An image processor 40 processes the image signal obtained from the first imaging means 3A (tracking camera) and the image signal obtained from the second imaging means 3B (fixed camera), generates image signals for display, and outputs them to the monitors 4A and 4B, respectively. In this embodiment, the monitors 4A and 4B simultaneously display the images of the first imaging means 3A (tracking camera) and the second imaging means 3B (fixed camera).

Figure 3:
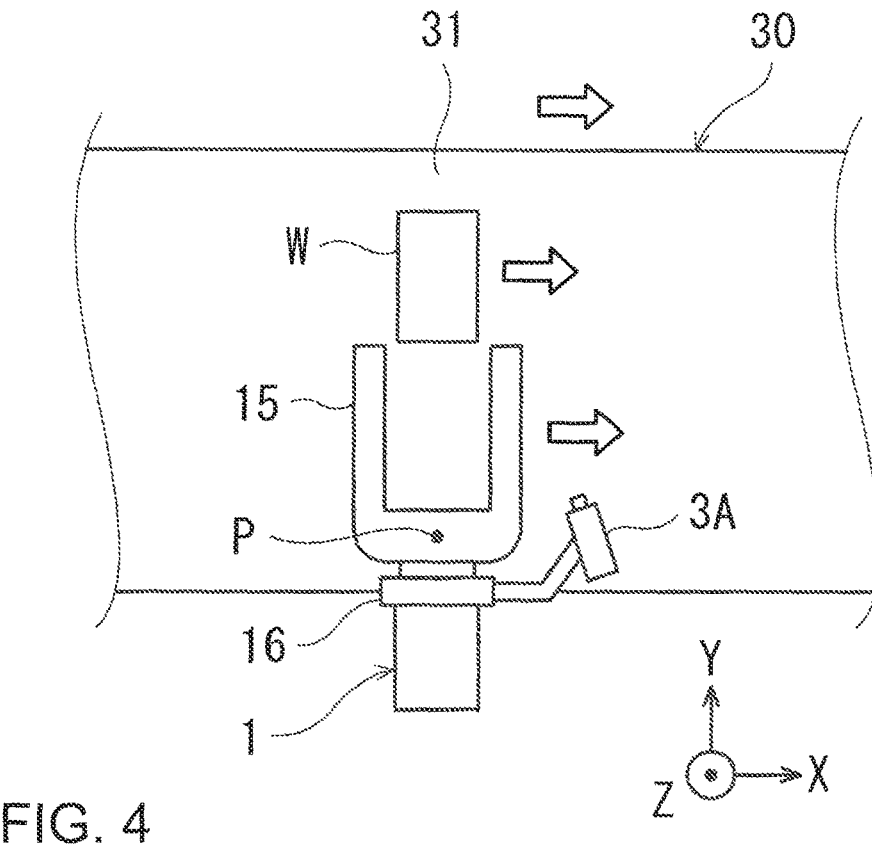
FIG. 3 is a plan view illustrating a situation of a tracking control of a robotic arm of FIG. 1.

Next, operation of the manipulator system 100 is described using the drawings. FIG. 3 is a plan view illustrating a situation of the tracking control of the robotic arm of FIG. 1. As illustrated in FIG. 3, the control device 5 first executes the automatic operation program to move the tool center point P at the tip end of the robotic arm 1 to the position and posture which are taught beforehand Note that, although the coordinate system is arbitrary, here, when the operator operates the robotic arm 1, the X-axis is set so that it is parallel to the ground and the conveying direction of the conveyor is the positive direction. In addition, the Y-axis is set so that it is parallel to the ground and along a direction perpendicular to the X-axis. In addition, the Z-axis is set along a direction perpendicular to the ground. Moreover, in FIG. 3, the workpiece W is disposed on the conveyor belt corresponding to the instructing position of the robotic arm 1. In the automatic operation, the operating instruction from the operating device 2 is not inputted into the control device 5. The control device 5 sets the target values of the position and posture at the tip end of the robotic arm 1 based on the automatic operation program and the sensor signals from the encoders 11a-14a, drives the motors M1-M5 to move the tip end of the robotic arm 1 to the teaching point (see FIG. 2).

Then, when the moving device 30 (conveyor) starts the operation and the conveyor belt 31 circulates the positive direction of the X-axis (the arrow direction of FIG. 3), the workpiece W placed on the conveyor belt 31 is conveyed in the positive direction of the X-axis. Here, the detection signal of the conveyor encoder 32a is inputted into the control device 5, and the control device 5 starts the tracking control. The control device 5 detects the moving amount of the workpiece W based on the detection signal inputted from the conveyor encoder 32a, and calculates the workpiece tracking amount at the tip end of the robotic arm 1 based on the moving amount of the workpiece W. The control device 5 adds the workpiece tracking amount at the tip end of the robotic arm 1 to the target values of the position and posture at the tip end of the robotic arm 1, and these are reflected on the current instruction values of the motors M1-M5 (see FIG. 2). Thus, the tip end of the robotic arm 1 is capable of tracking the workpiece W being conveyed by the conveyor.

Figure 4:
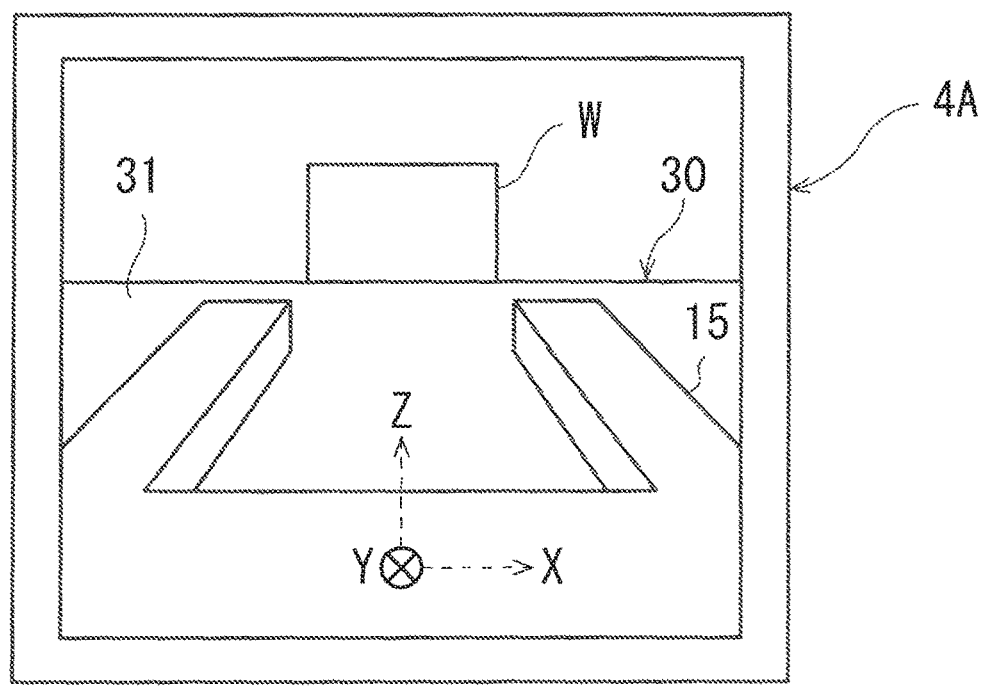
FIG. 4 is one example of a monitoring screen which displays an image imaged by a first imaging means.

Meanwhile, the first imaging means 3A at the tip end of the robotic arm 1 images the situation at the tip end of the robotic arm 1 which is subject to the tracking control. FIG. 4 illustrates one example of the monitoring screen which displays the image imaged by the first imaging means 3A. As illustrated in FIG. 4, the situation at the tip end of the robotic arm 1 which is subject to the tracking control is displayed on the screen of the monitor 4A. In the screen, the tool 15 located at the tip end of the robotic arm 1, the conveyor located forward thereof, and the workpiece W on the conveyor are displayed. During the robotic arm 1 following after the workpiece W, the worker 80 operates the operating device 2 while looking at the monitoring screen to operate the tool 15 at the tip end of the robotic arm 1. Since the robotic arm 1 follows after the moving workpiece W, the workpiece W seems to be stopped in the image imaged by the first imaging means (camera) 3A. The worker is easy to operate the robot hand (the tool 15) with the operating device 2. The workpiece W is able to be gripped by the robot hand.

Figure 5:
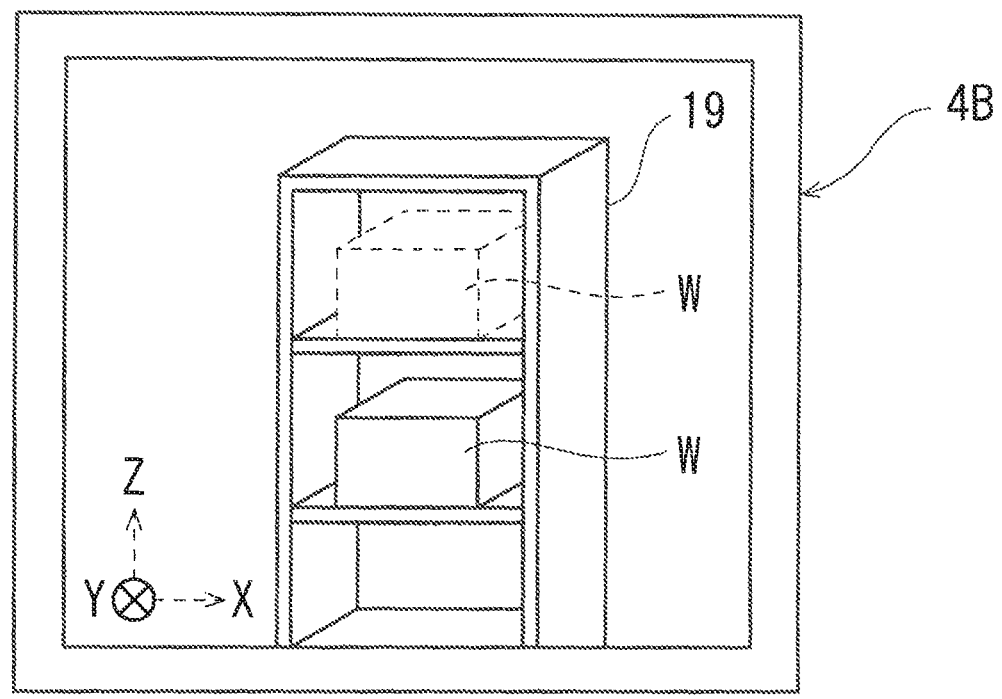
FIG. 5 is one example of a monitoring screen which displays an image imaged by a second imaging means.

Next, the worker switches the control of the robotic arm 1 from the tracking control to the manual control after gripping the workpiece W by the robot hand. The switching of the control may be, for example, performed manually by operating the operating device 2, or performed automatically. In the manual control, the operation of the robotic arm 1 is controlled only according to the operating instruction generated by the operating device 2. FIG. 5 illustrates one example of the monitoring screen which displays the image imaged by the second imaging means 3B. Here, since the second imaging means 3B is fixedly installed to the ceiling 90, and is oriented toward the storage shelf 19, the situation around the storage shelf 19 is displayed on the screen of the monitor 4B. The second imaging means 3B images the situation of the work to convey the workpiece W from the conveyor to near the storage shelf 19 by the robot hand between the conveyor and the storage shelf 19 of the workpiece W. The worker stores the workpiece W gripped by the robot hand at a given position inside the storage shelf 19 by operating the operating device 2 while checking the situation around the storage shelf 19 on the screen of the monitor 4B. Thus, the handling work of the weighted workpiece being conveyed by the conveyor is capable to be performed with sufficient accuracy.

[Modification: Moving Device]

Figure 6:
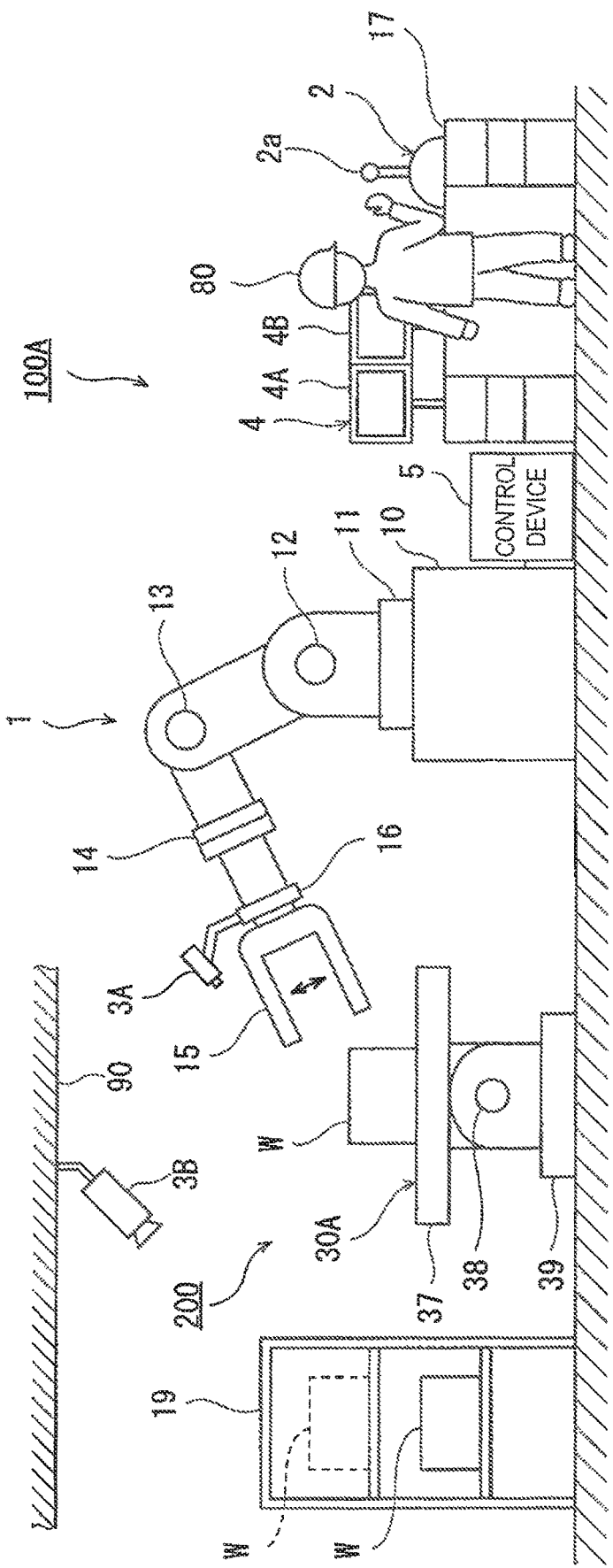
FIG. 6 is a schematic view illustrating a manipulator system according to a modification of the first embodiment.

Note that, in the first embodiment, although the moving device 30 is the conveyor, it may be, for example, a positioner, which is provided with one or more driving shafts, and is a device capable of moving the workpiece W. FIG. 6 is a schematic view illustrating a manipulator system 100A according to a modification of the first embodiment. As illustrated in FIG. 6, in this modification, a moving device 30A includes a rotary table 37 where the workpiece W is placed, a rotating shaft 38, and a base 39. The rotating shaft 38 is provided with a drive motor (not illustrated), and rotates the rotary table 37 with respect to the rotating shaft 38. A positioner encoder 38a which detects a driving amount of the rotating shaft 38 is attached to the drive motor, and is configured to output a detection signal to the control device 5. Thus, the moving device 30A is a positioner which rotates the workpiece W with respect to the rotating shaft 38. Alternatively, the positioner may be configured, for example, to translate the workpiece W with respect to a linear-movement shaft.

Second Embodiment

Next, a second embodiment is described. Below, description of the configuration common to the first embodiment is omitted, and only different configuration is described.

Figure 7:
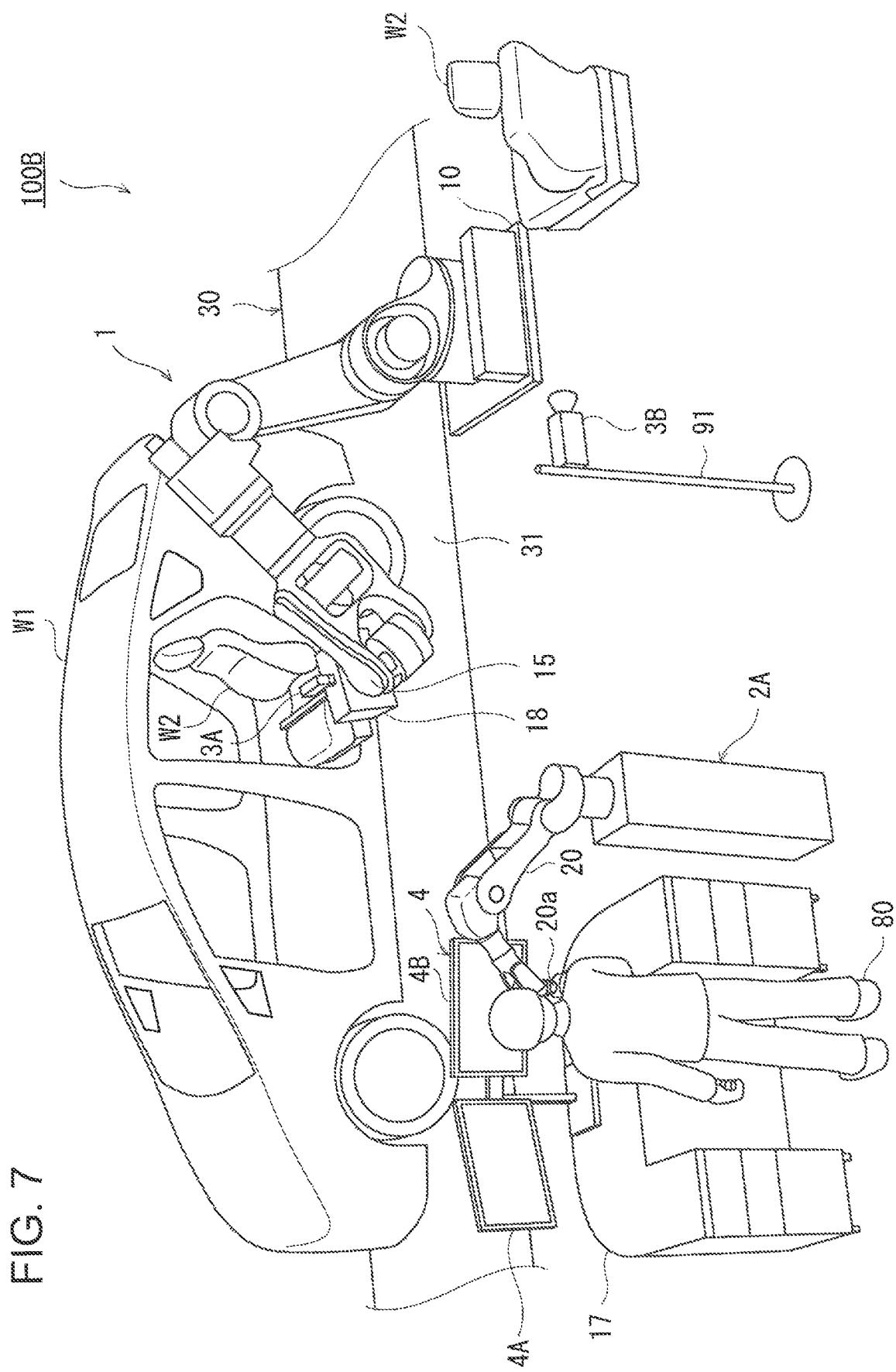
FIG. 7 is a schematic view illustrating a manipulator system according to a second embodiment.

FIG. 7 is a schematic view illustrating a manipulator system according to the second embodiment. As illustrated in FIG. 7, a manipulator system 100B of this embodiment grips a seat (a workpiece W2), and performs an assembling of the seat (the workpiece W2) to a vehicle body frame (a workpiece W1) of an automobile being conveyed by the conveyor (the moving device 30).

Moreover, the second imaging means (fixed camera) 3B of this embodiment is fixedly installed to a post 91 which stands near the moving device 30 (the conveyor) in the work area. Here, the second imaging means 3B is oriented toward the seat (the workpiece W2), and images the situation of the work to grip the workpiece W2 by the robot hand (the tool 15). That is, the second imaging means 3B images the situation of the work to convey the seat (the workpiece W2) from a given position to near the conveyor by the robot hand between the floor (the given position) where the seat (the workpiece W2) is placed and the conveyor. Note that a plurality of second imaging means 3B may be installed. For example, another second imaging means 3B may image the situation of the entire work area.

Figure 8:
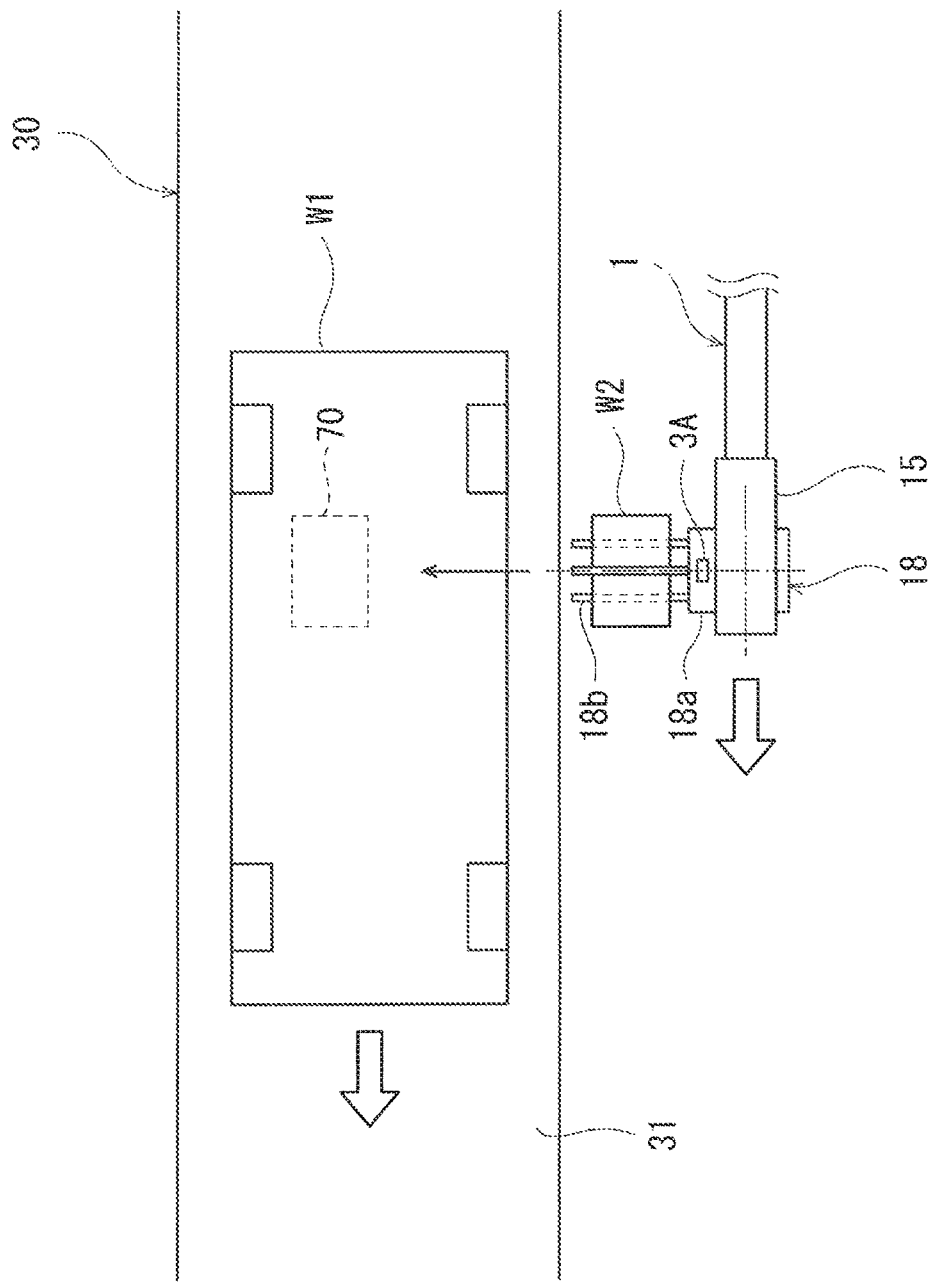
FIG. 8 is a plan view illustrating a configuration of a robotic arm of FIG. 7 which grips a workpiece.

The tool 15 of this embodiment includes a fixing tool 18 which is gripped by the robot hand attached to the tip end of the robotic arm 1, and supports the seat (W2). FIG. 8 is a plan view illustrating a configuration of the robotic arm 1 which grips the seat (W2). As illustrated in FIG. 8, the fixing tool 18 has a main body part 18a which is gripped by the robot hand, and three claw parts 18b projecting in a longitudinal direction of the main body part 18a. Here, the first imaging means 3A is attached to the main body part 18a. One of the three claw parts 18b projects from an upper position of the main body part 18a, other two parts project from positions which are below the projected position of the first claw part of the main body part 18a. The other two claw parts are located at the same height and separated from each other by a given distance. Thus, the seat (W2) is fixable between the three claw parts 18b.

In this embodiment, the worker first grips the seat (W2) by the robot hand by operating an operating device 2, while checking the image imaged by the second imaging means 3B on the displaying means 4. Next, the worker switches the control of the robotic arm 1 from the manual control to the tracking control. FIG. 8 illustrates the situation of the tracking control of the robotic arm 1 which grips the workpiece W2. As illustrated in FIG. 8, the control device 5 detects the moving amount of the vehicle body frame (W1) based on the driving amount of the driving shaft of the conveyor, and carries out the tracking control of the robotic arm 1 so that the longitudinal directions of the robot hand becomes parallel to the longitudinal directions of the vehicle body frame (W1), and the longitudinal direction of the fixing tool 18 becomes perpendicular to the longitudinal directions of the vehicle body frame (W1), according to the moving amount of the vehicle body frame (W1). Thus, only the fixing tool 18 which supports the seat (W2) is insertable into the vehicle body frame (W1), together with the seat (W2) so that the seat (W2) is easier to be attached to an attaching position 70. Thus, the seat (W2) can suitably be assembled to the vehicle body frame (W1) on the conveyor, while carrying out the tracking control of the robotic arm 1.

Moreover, the operating device 2A of this embodiment is provided with a master arm 20 which has a similarity structure to the robotic arm 1 as a slave arm (see FIG. 6). Here, the "similarity structure" includes both a case where the arm contours are similar and a case where the arm joint structures are similar. Thus, the worker is able to perform an instinctive operation by directly operating a tip-end part 20a of the master arm 20. Therefore, the accuracy of the work improves.

[Modification]

Figure 9:
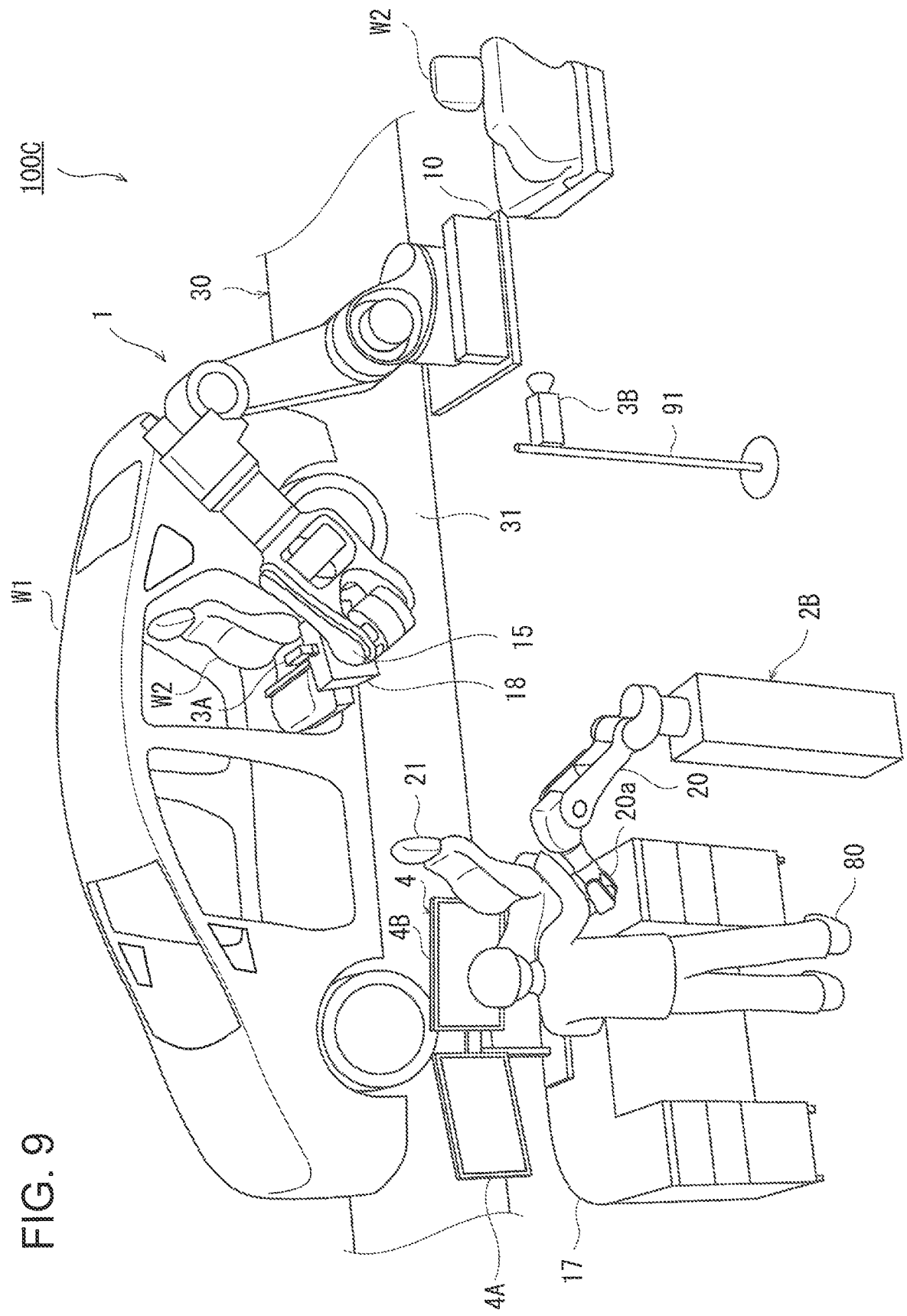
FIG. 9 is a schematic view illustrating a manipulator system according to a modification of the second embodiment.

Note that, although the operating device 2A is configured to have the master arm 20 in the second embodiment, it is not limited to this structure. FIG. 9 is a schematic view illustrating a manipulator system 100C according to a modification of the second embodiment. As illustrated in FIG. 9, anoperating device 2B is provided at the tip-end part 20a of the master arm 20 with a dummy workpiece 21 to be worked by the master arm 20. Here, the shape of the dummy workpiece 21 has a similar shape to the seat (W2) of the automobile. Thus, the worker is able to perform a more instinctive operation by directly operating the dummy workpiece 21.

Other Embodiments

Note that, in the above embodiments, although the image of the first imaging means 3A (tracking camera) and the image of the second imaging means 3B (fixed camera) are configured to be displayed simultaneously, the image imaged by the first imaging means 3A and the image imaged by the second imaging means 3B may be switchingly displayed. In this case, the image processor is configured to switchingly output to the monitor the image signal from the tracking camera and the image signal from the fixed camera, according to the operating signal inputted from the operating device. The worker suitably switches the screen display according to the work situation. Thus, the monitor switchingly displays the image of the situation of the work to the workpiece, imaged by the tracking camera following the movement of the workpiece, and the image of the situation of the work to convey the workpiece between the given position and the conveyor in the work area, imaged by the fixed camera.

Figure 10:
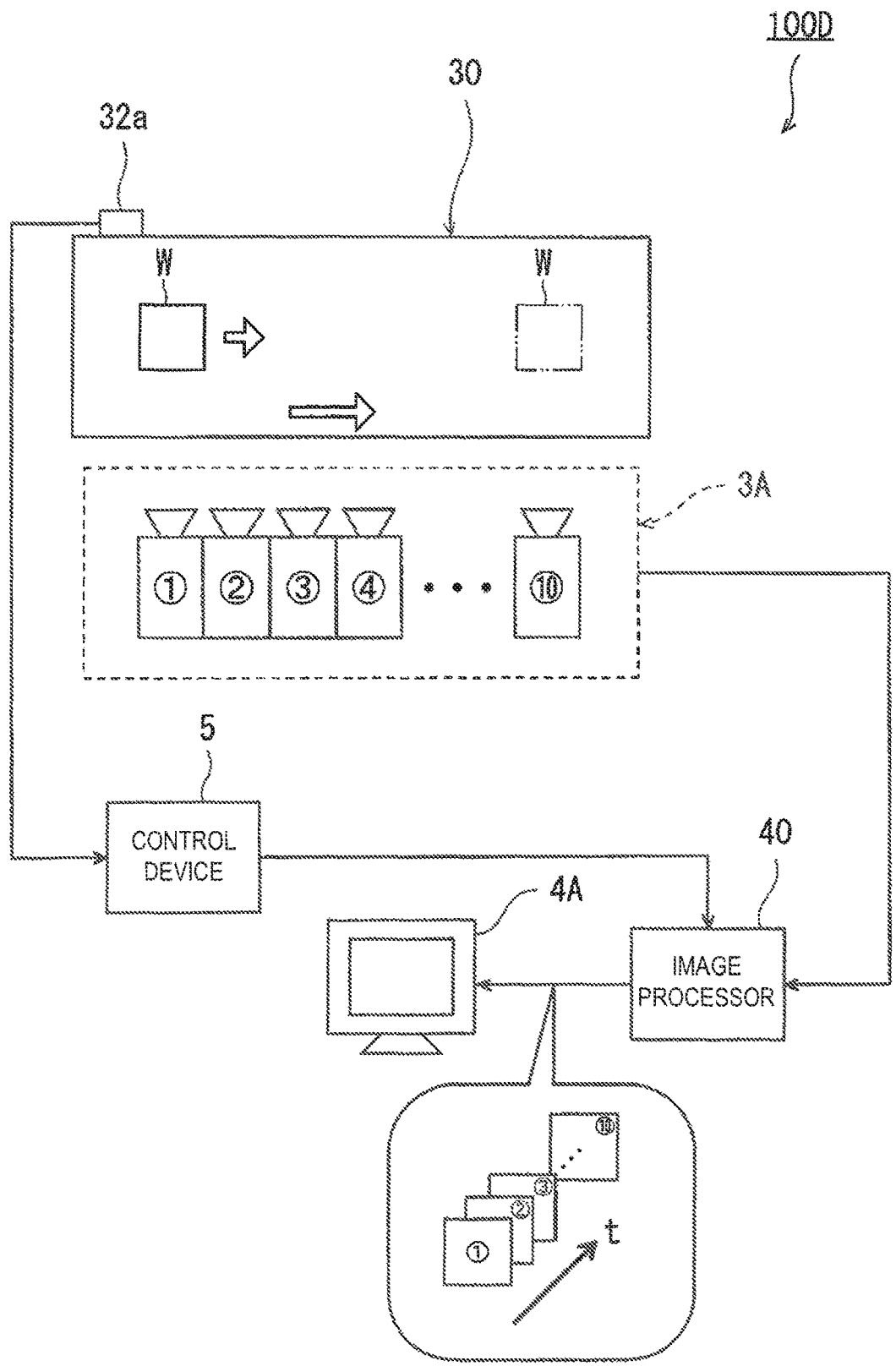
FIG. 10 is a schematic view illustrating a manipulator system according to another embodiment.

Note that, in the above embodiments, although the first imaging means 3A is attached to the tip end of the robotic arm 1, it may be attached to the conveyor belt 31 (FIG. 1) of the conveyor which is the moving device 30, or the rotary table 37 (FIG. 6) of the positioner, as long as it is oriented in the imageable direction of the workpiece W. FIG. 10 is a schematic view illustrating a manipulator system 100D according to another embodiment. As illustrated in FIG. 10, the first imaging means 3A of this embodiment is a plurality of fixed cameras which are arrayed along the moving direction of the moving device 30 (in the arrow direction in this figure). Here, ten fixed cameras are arrayed along the conveying direction of the moving device 30 (the conveyor). The image signals imaged by the plurality of fixed cameras are transmitted to the image processor 40. The control device 5 is configured to control an output timing of the image signal from each fixed camera according to the detection signal from the conveyor encoder 32a. The image processor 40 outputs the image signal to the monitor 4A based on the control instruction from the control device 5, while sequentially switching the output timings of the image signals imaged by the plurality of fixed cameras so that the image follows the movement of the workpiece W. With such a configuration, the workpiece W is also imageable while following the movement of the workpiece W. That is, the workpiece W seems to be stopped in the image displayed on the monitor 4A by sequentially switching between the plurality of fixed cameras of the first imaging means 3A.

Note that the control device 5 may be configured to control the operations of the plurality of fixed cameras according to the detection signal from the conveyor encoder 32a, and the operating timings of the plurality of fixed cameras may be switched sequentially so that the movement of the workpiece W is followed.

Note that, in the above embodiments, although the work of the robotic arm 1 is the handling work of the weighted workpiece, or the rigging work of the automobile, it is not be limited to these works, as long as the work involves the movement of the workpiece which a human is not good at. The work by the robotic arm 1 may be an assembly work of robots, or may be a paint work. For example, in the case of the assembly work of the robots, components, such as a transmission and a motor, are attached to the robotic arm being conveyed at a fixed speed. For example, in the painting process of accessories, a workpiece suspended from a hanger moving at a fixed speed is painted by manipulation. Alternatively, the work may be an arc-welding work, or a similar adhesives application work. For example, in the arc welding, although a welding tool is controlled at a low but fixed speed, the automatic operation while being corrected according to a sensor may be difficult when the workpiece is not uniform, or when the environment is bad. Therefore, in such a case, the positional correction is possible while maintaining the tool at the fixed speed with respect to the workpiece, by the worker applying a manipulating operation only in a direction perpendicular to the moving direction of the tool while checking the work status by the camera.

Note that, in the above embodiments, although the second imaging means 3B (fixed camera) is fixed to the ceiling 90 or the post 91, it is not limited to these structures, as long as it is fixedly provided in the work area 200 to image the situation of the work.

Note that, in the above embodiments, although the robotic arm 1 of this embodiment is the single arm type, it may be a double arm type which is driven coaxially. Thus, since the installation space is small and a similar work to a fine manual work by a human is able to be performed, the robot is easily replaceable with the human in the production line.

From the above description, it is apparent for a person skilled in the art that many improvements and other embodiments of the present disclosure are possible. Therefore, the above description is to be interpreted only as illustration, and it is provided in order to teach a person skilled in the art the best mode which implements the present disclosure. Details of both or one of the structures and the functions of the present disclosure may be substantially changed without departing from the spirit of the present disclosure.

INDUSTRIAL APPLICABILITY

The present disclosure is useful to the manipulator system which performs the work to the workpiece being moved by the conveyor etc.

DESCRIPTION OF REFERENCE CHARACTERS

1 Robotic Arm
2, 2A, 2B Operating Device
2a Joystick
3A First Imaging Means (Tracking Camera)
3B Second Imaging Means (Fixed Camera)
4 Displaying Means
4A, 4B Monitor
5 Control Device
10 Base
11-14 Joint
Tool
11a-15a Encoder
16 Tool Attaching Part
17 Desk
18 Fixing Tool
19 Workpiece Storage Shelf
20 Master Arm
21 Dummy Workpiece
30, 30A Moving Device (Conveyor, Positioner)
31 Conveyor Belt
32 Driving Pulley (Driving Shaft)
32a Conveyor Encoder
33 Driven Pulley (Driven Shaft)
34 Conveyor Control Device
37 Rotary Table
38 Rotating Shaft
38a Positioner Encoder
39 Base
40 Image Processor
51 Arithmetic Processor
52 Motor Controller
53 Memory
55 Motor Rotation Amount Detecting Module
56 Workpiece Moving Amount Detecting Module
61 Position-posture Calculating Module (Automatic Operation)
62 Position-posture Calculating Module (Workpiece Position Tracking)
63 Position-posture Calculating Module (Operating Device)
64 Inverse Transform Calculating Module
65, 66 Adder
80 Worker
90 Ceiling
91 Post
100 Manipulator System
200 Work Area
M1-M5 Motor
W, W1, W2 Workpiece

What is claimed is:

1. A manipulator system configured to perform a work to a workpiece being moved by a moving device, comprising:
   a robotic arm, having one or more joints and to which a tool configured to perform the work to the workpiece is attached;
   a first imaging means configured to image the workpiece, while following a movement of the workpiece;
   a second imaging means fixedly provided in a work area to image a situation of the work to the workpiece;
   a displaying means configured to display, to a worker, a first image imaged by the first imaging means and a second image imaged by the second imaging means;
   an operating device configured to be operated by the worker and receive a manipulation input, the worker operating the operating device to perform manipulation of the robotic arm while viewing the first image and the second image displayed by the displaying means; and
   a control device configured to:
   detect a moving amount of the workpiece being moved by the moving device;
   generate a tracking-controlled operation that is an operation of causing the robotic arm to follow the workpiece according to the detected moving amount of the workpiece; and
   add, to the tracking-controlled operation, a manipulation-controlled operation that is an operation of the robotic arm according to an operating instruction corresponding to the manipulation input to the operating device so as to control the robotic arm, such that the robotic arm performs the manipulation-controlled operation while performing the tracking-controlled operation.

2. The manipulator system of claim 1, wherein the manipulator system performs the work to the workpiece being moved by a conveyor or a positioner provided with one or more driving shafts, and
   wherein the control device detects the moving amount of the workpiece based on a driving amount of the one or more driving shafts of the conveyor or the positioner.

3. The manipulator system of claim 1, wherein the first imaging means is attached to a tip end of the robotic arm.

4. The manipulator system of claim 1, wherein the displaying means switchingly displays the first image imaged by the first imaging means and the second image imaged by the second imaging means.

5. The manipulator system of claim 4, wherein the displaying means switchingly displays the first image of the situation of the work to the workpiece imaged by the first imaging means while following the movement of the workpiece, and the second image of the situation of the work to convey the workpiece between a given position and the moving device in the work area, imaged by the second imaging means.

6. The manipulator system of claim 1, wherein the first imaging means includes a plurality of fixed cameras fixedly provided in the work area and arrayed along the moving direction of the moving device, the first image being one of a plurality of first images captured by the plurality of fixed cameras, and wherein the displaying means switchingly and sequentially displays the plurality of first images imaged by the plurality of fixed cameras so as to follow the movement of the workpiece.

7. The manipulator system of claim 1, wherein the control device detects the moving amount of the workpiece, which is moved by the moving device, based on a driving amount of the moving device, and controls the operation of the robotic arm based on the operating instruction of the operating device.

8. The manipulator system of claim 1, wherein the control device controls the operation of the robotic arm based on a third moving amount of a position and posture at a tip end of the robotic arm, the third moving amount being a sum of a first moving amount of the position and the posture at the tip end of the robotic arm and a second moving amount of the position and the posture at the tip end of the robotic arm, the first moving amount being a moving amount by which the robotic arm follows the workpiece according to the moving amount of the workpiece, the second moving amount being a moving amount by which the robotic arm operates based on the operating instruction of the operating device.

9. A manipulator system configured to perform a work to a workpiece being moved by a conveyor, comprising:

a robotic arm, having one or more joints and to which a tool configured to perform the work to the workpiece is attached;

a first camera configured to image the workpiece, while following a movement of the workpiece;

a second camera fixedly provided in a work area to image a situation of the work to the workpiece;

a display configured to display, to a worker, a first image imaged by the first camera and a second image imaged by the second camera; and a joystick configured to be operated by the worker and receive a manipulation Input, the worker operating the joystick to perform manipulation of the robotic arm while viewing the first image and the second image displayed by the display; and a processor programmed to:

detect a moving amount of the workpiece being moved by the conveyor;

generate a tracking-controlled operation that is an operation of causing the robotic arm to follow the workpiece according to the detected moving amount of the workpiece; and add, to the tracking-controlled operation, a manipulation-controlled operation that is an operation of the robotic arm according to an operating instruction corresponding to the manipulation input to the joystick so as to control the robotic arm, such that the robotic arm performs the manipulation-controlled operation while performing the tracking-controlled operation.

* * * * *